United States Patent [19]

Lanzoni

[11] Patent Number: 4,625,554

[45] Date of Patent: Dec. 2, 1986

[54] DEVICE FOR TIGHTENING A NUT ON A FASTENING PIN OF A NUCLEAR REACTOR GUIDING TUBE

[75] Inventor: Maurice Lanzoni, Cergy, France

[73] Assignee: Framatome & Cie., Courbevoie, France

[21] Appl. No.: 715,448

[22] Filed: Mar. 25, 1985

[30] Foreign Application Priority Data

Mar. 23, 1984 [FR] France .................. 84 04511

[51] Int. Cl.⁴ .................................... G01N 29/00
[52] U.S. Cl. ................................ 73/581; 73/862.21
[58] Field of Search ............... 73/581, 597, 862.21, 73/761; 376/245, 249, 252

[56] References Cited

U.S. PATENT DOCUMENTS 3,969,810  7/1976  Pagano .......................... 73/581

FOREIGN PATENT DOCUMENTS 2444267  7/1980  France .
2542869  9/1984  France .
52-73781  6/1977  Japan .

OTHER PUBLICATIONS

*Machine Design*, "Ultrasonic Pulser Reveals Bolt Preload", vol. 50, No. 28, p. 52, Dec. 1978.

*Primary Examiner*—Stephen A. Kreitman
*Attorney, Agent, or Firm*—Pollock, Vande Sande & Priddy

[57] ABSTRACT

A tightening wrench (5) carrying a measuring cell (8) freely mounted in the hollow part (4) of a wrench (5) and adapted to bear against an end of the pin (2) subjected to the pretension. A detector emitting and receiving ultrasounds (21) disposed inside the measuring cell (8) is made to bear against the end of the pin (2) by a spring (25) interposed between the cell (8) and the detector (21). The cell (8) itself bears against the end of the pin (2) through the action of a leaf spring (9) carried by the wrench (5).

3 Claims, 3 Drawing Figures

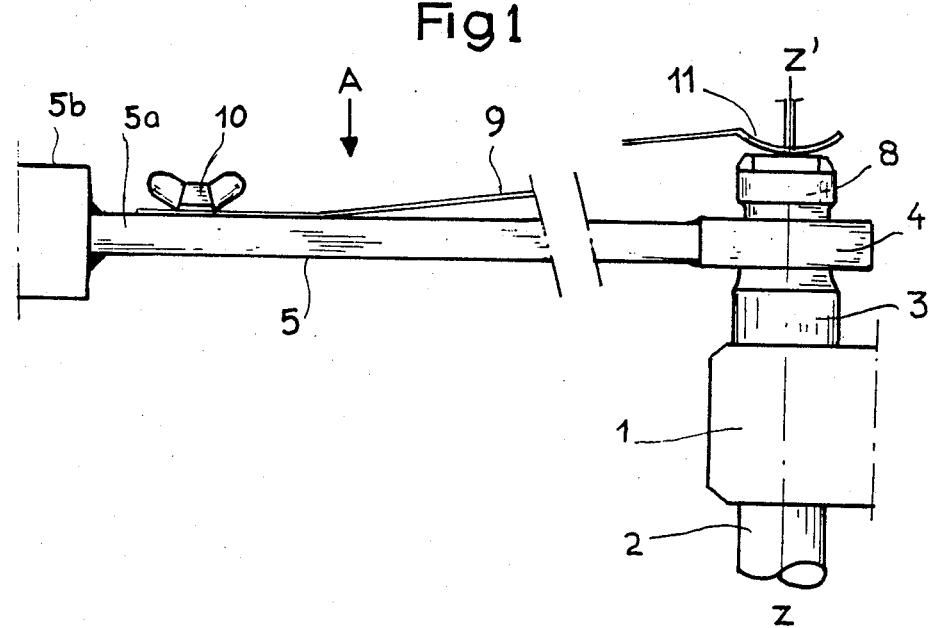
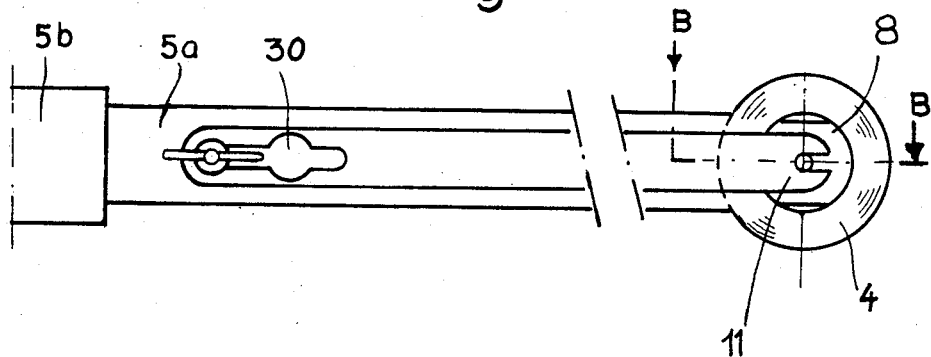

DEVICE FOR TIGHTENING A NUT ON A FASTENING PIN OF A NUCLEAR REACTOR GUIDING TUBE

FIELD OF THE INVENTION

The invention relates to a device for tightening a nut on a fastening pin of a guiding tube of a nuclear reactor with a checking of the pretension of one of the elements of the connection.

BACKGROUND OF THE INVENTION

Pressurized water nuclear reactors contain a core consisting of assemblies in which the neutron reactions giving rise to the power released by the core take place. In order to control this power, in certain core assemblies control rods of neutron-absorbing material are displaced in the vertical direction over the entire height of the assemblies. The control rods formed by bundles of absorbing rods of great length are guided by members extending in line with the guiding tubes of the assemblies into which the control rods are introduced, and disposed above the core. These members are disposed inside guiding tubes forming part of the upper internal equipment of the nuclear reactor. These guiding tubes are fixed to the top core plate with the aid of pins provided with a screw thread, onto which is screwed a nut which comes to bear against the foot of the guiding tube. The pin is in turn fixed inside the top core plate by its bottom part.

In the operation of pressurized water nuclear reactors, it has been found that the mechanical properties of the pins fastening the feet of guiding tubes of the upper internal equipment may deteriorate after a certain period of operation of the reactor. In some cases, fractures of these fastening pins could even be observed. It was possible to attribute these defects to inadequate tightening of the screwed connection between the fastening pins and the foot of the guiding tube. If the tightening is too slack, the guiding tube is not perfectly immobilized, and this defect increases during the operation of the reactor, in the course of which the guiding tubes are subjected to the circulation of pressurized water at high temperature and with a very high rate of flow.

In cases where the tightening of the pins is excessive, the tensile stresses in the pin give rise to stress corrosion of the latter.

In the first case, fatigue fractures occur, and in the second case fractures are caused by cracking due to corrosion.

For the purpose of mounting the fastening pins on the feet of the guiding tubes, the nuts are tightened on the pins by hand with the aid of a torque wrench. The accuracy achieved in respect of tightening torque is insufficient to enable the tightening defects described above to be avoided.

PRIOR ART

It has already been proposed to check the pretension of a screwed connection by ultrasonic measurement of the elongation of a member of the connection which is subjected to a tensile load during the tightening. The devices used comprise a detector which emits and receives ultrasounds and is disposed in a measuring cell connected to the wrench, so that the detector turns with the wrench during the tightening. Such a device may be used under good conditions when the member (screw or bolt) on which the measurement is carried out turns during the tightening. This is not so when this member is fixed during the tightening, such as the fixing pin for a guide tube: the detector then turns on the end of the pin, and this is liable to result in errors in the measurement and in a deterioration of the detector. A continuous measurement of the pretension of the pin during the tightening of the nut is then difficult, if not impossible. In the case where the detector turns with the wrench, there is also a danger of producing harmful twisting or bending of the measuring cables during the tightening.

OBJECT OF THE INVENTION

The object of the invention is therefore to propose a device for tightening a nut on a fastening pin for a guiding tube of a nuclear reactor, comprising a wrench having a hollow profiled part having a shape corresponding to the shape of the nut, and means for checking the pretension of the pin comprising a detector emitting and receiving ultrasounds and placed within a measuring cell disposed in the hollow part of the wrench, this device permitting the very precise measurement of the pretension during the actual tightening operation.

SUMMARY OF THE INVENTION

For this purpose, this cell is freely mounted in the hollow part of the wrench and has a part of small diameter which is less than the inside diameter of the nut, the lower part of this small-diameter part bearing on the end of the pin in the operating position of the tool, so that the detector is put into contact with the end of the pin for the measurement, and a part of large diameter whose diameter exceeds the inside diameter of the hollow part of the wrench and is intended to bear against the wrench for the withdrawal and the transporting of the tool from a working position to another position, and the device further comprises resiliently yieldable means carried by the wrench for exerting a bearing force directed along the axis ZZ' of tightening on the measuring cell without the wrench being capable of driving the measuring cell in rotation during the tightening.

BRIEF DESCRIPTION OF THE DRAWINGS

In order to enable the invention to be well understood, a description will now be given, as a nonlimitative example and with reference to the accompanying drawings, of one embodiment of a tightening device according to the invention, adapted to the case of the tightening of the nuts of pins for fastening guiding tubes on the upper core plate of a pressurized water nuclear reactor.

FIG. 1 is a side elevation of the tightening device in the working position on a guiding tube fastening pin.

FIG. 2 is a plan view, in the direction A, of the device shown in FIG. 1.

DETAILED DESCRIPTION

Figure 3:
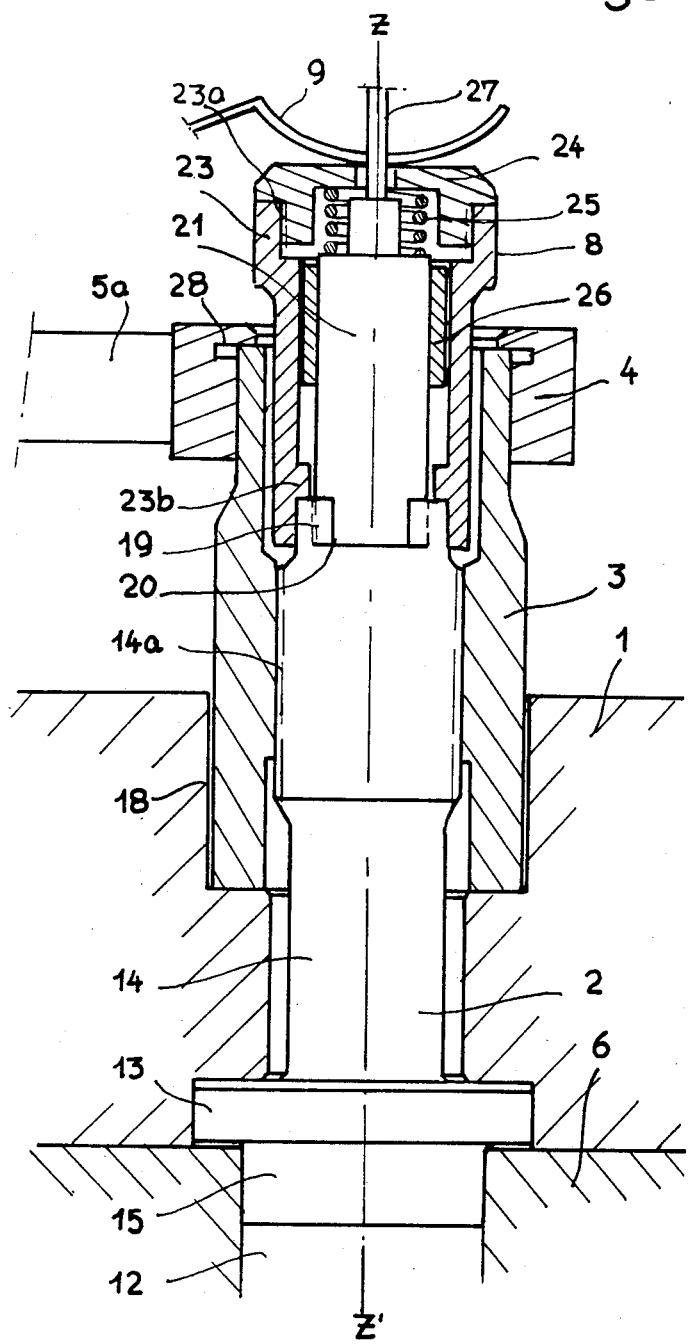
FIG. 3 is a view in section on the line B—B shown in FIG. 2.

In FIGS. 1 and 2 show the foot 1 of a guiding tube provided with a hole for fastening a pin 2 with the aid of a nut 3. The tightening tool is a wrench whose profiled hollow part 4 comes to engage over a corresponding profiled part of the nut 3 in order to turn the nut about the tightening axis Z—Z'. This tightening wrench 5 also comprises an arm 5a and a handle 5b.

A tightening torque measuring cell 8 is disposed inside the hollow part 4 of the wrench, in the direction of the tightening axis Z—Z'. A leaf spring 9 fixed on the arm 5a of the wrench with the aid of a wing nut 10 has a curved end portion 11 which comes to bear against the top end of the load cell 8.

Referring to FIG. 3, it can be seen that the pin 2 comprises, in addition to its bottom part 12 intended to engage in the bottom core plate 6, a widened support portion 13 and a stem 14 having a threaded portion 14a onto which the nut 3 is to be screwed.

The bottom portion 12 of the fastening pin 2 has a diameter slightly larger than the bore 15 in the core support plate 6 in which it is engaged, a slot in this portion 12 of the fastening pin permitting elastic deformation at the moment when the guiding tube, equipped with its fastening pins, is placed in position. The fastening pin is in turn fixed on the foot 1 of the guiding tube by the nut 3, which comes to bear against the foot 1 inside a widened bore 18 provided in its top part, as an extension of the bore for the passage of the stem 14 of the fastening pin 2 in the foot 1. The tool shown in FIGS. 1 and 2 makes it possible to effect and to check the tightening of the nut 3 enabling the fastening pin to be fixed on the foot 1 of the guiding tube.

The top part of the stem 14 of the pin 2, above the threaded portion 14a, has a smaller diameter than the portion 14a and has formed in it a bore 19 and a diametrical slot 20 of the same depth as the bore 19. This portion of the stem 14, corresponding to the top end of the fastening pin 2, constitutes the support zone for the measuring cell 8 containing an ultrasonic transmitter and receiver detector 21 on the end of the fastening pin.

The load cell 8 comprises a sleeve 23, the inside surface of which is machined to form an internal screw thread 23a at the top and a shoulder 23b at the bottom. When the tool is in position on the nut 3, during the tightening of the nut, the shoulder 23b comes to bear against the top part of the stem 14 of the pin 2. The internal screw thread 23a permits the fastening of the closure cap 24 of the load cell 8. This cap 24 has an opening formed in it for the passage of the supply and measuring cable 27 associated with the detector 21, which extends in the direction of the axis of the load cell 8. The detector 21, of cylindrical shape, is free for translatory movement inside the cell 8 and by its bottom part is supported inside the bore 19 during the tightening of the nut 3 with the aid of the tool 5. On the outside diameter of the detector 21 is tightly held a retaining ring 26 constituting stop means which prevents the detector from becoming detached from the load cell 8 when the latter and the tightening tool are removed after the fastening of the pin has been completed. The ring 26 then comes to bear against the shoulder 23b.

Between the top surface of the transmitter-receiver detector 21 and the inside surface of the cap 24 of the cell 8 is interposed a spring 25 making it possible to exert a perfectly controlled force in the direction Z—Z' on the detector supported in the bore 19 in the stem 14 of the pin 2 during the tightening of the nut 3.

The internal hexagonal part 4 of the wrench 5, wich comes to engage over the corresponding external hexagonal part of the nut 3, is provided with a stop lip 28 making it possible to achieve perfect positioning of the wrench on the nut 3.

The principle of measurement of the tightening torque is as follows: ultrasound is transmitted by the detector 21 into the stem 14 of the screw in the axial direction Z—Z', is reflected on the slot between the resilient branches 12 of the pin 2, and picked up on its return by the transmitter-receiver detector 21. A precise measurement of the propagation time of the ultrasound makes it possible to determine the variations of length of the stem 14 of the pin during the tightening of the nut 3. This elongation is in turn dependent on the stresses in the stem 14 and therefore on the pretension of the stem 14.

Previous calibration makes it possible to link the ultrasound propagation time to the elongation or pretension on the stem 14.

For the purpose of tightening a nut 3 on a pin 2, the hollow end portion 4 of the wrench 5 is placed over the nut 3 in the position shown in FIG. 3. The load cell 8 resting in the opening of the part 4 of the wrench comes to bear by its shoulder 23b against the end of the stem 14 when the nut has reached the position in which it abuts against the bottom of the bore 18, as shown in FIG. 3. The cell 8 is then firmly held against the end of the stem 14 by the leaf spring 9, in contact with the cell 8 by its support surface 11. The sleeve 23 is also provided with a stud on its inner surface to engage in the slot 20 provided in the end portion of the pin 2 when the load cell 8 is placed in position. The sleeve 23 is thus locked in respect of rotation on the pin 2.

A certain adjustment of the length of the spring 9 is possible with the aid of an oblong opening 30 provided at the end of the leaf spring 9 where the tightening is effected with the aid of the wing nut 10. The outside diameter of the sleeve 23 of the cell 8 is smaller than the inside diameter of the top part of the nut 3. When the cell is resting on the end of the stem 14, this cell is entirely independent of the end portion 4 of the wrench, so that the cell 8, locked in respect of rotation by the stud on the sleeve 23, remains completely motionless during the tightening of the nut. The leaf spring 9 transmits its support force in the direction Z—Z' to the cell 8 by way of the curved surface 11.

The casing cover 24 is screwed and clamped on the casing. The spring 9 therefore has a relative movement of rotation under slight friction in relation to the cover.

The ultrasonic detector 21 in turn remains motionless and supported with perfectly controlled pressure through the action of the spring 25 on the end of the stem 14.

It is therefore possible to make length measurements by ultrasound under very good conditions during the tightening.

At the end of the tightening operation, when the tool is removed, the detector 21 falls back until the ring 26 comes to bear against the shoulder 23b and the cell 8 comes to rest by its widened top part against the support lip 28 of the portion 4 of the wrench 5.

The pretension checking device is therefore placed in position automatically and without difficulty at the moment when the wrench is placed over a nut, while nevertheless this measuring cell remains motionless and perfectly supported on the stem of the pin during the tightening.

Moreover, the ultrasonic detector 21 is likewise placed in position by the same operation and remains motionless and bearing with constant pressure against the end of the pin during the tightening.

It can therefore be seen that the principal advantages of the device according to the invention are the fact that it permits accurate and effective checking of the pretension of the screw by a very simple operation which is carried out automatically when use is made of the tool to effect the tightening of the screwed connection.

The elongation of the stem of the screw may be displayed digitally on a screen, and an indication may be given at the moment when optimum elongation has been achieved.

The forces by which the measuring cell of the ultrasonic detector bear against the end of the stem of the pin may be obtained by means other than leaf or coil springs, such as have been described.

It is also possible to conceive the construction of the measuring cell, and its association with the tightening wrench, in a different manner from that described above.

I claim:

1. A device for tightening a nut on a fastening pin of a guiding tube of a nuclear reactor, comprising in combination a wrench having a hollow profiled part which has an axis constituting a tightening axis and a shape corresponding to the shape of the nut, and means for checking the pretension of the pin comprising a measuring cell disposed in the hollow part of the wrench, a detector transmitting and receiving ultrasounds placed inside the cell, the cell being freely mounted in said hollow part of the wrench and comprising a portion of small diameter whose diameter is less than an inside diameter of the nut, a lower portion of the small-diameter portion of the cell being provided for coming to bear against an end of the pin in an operating position of the device so that the detector is put into contact with said end of the pin for the measurement, the cell further comprising a portion which is of large diameter which exceeds an inside diameter of the hollow part of the wrench and is provided for bearing against the wrench for withdrawal and the transporting of the device from a working position to another position, the device further comprising resiliently yieldable means carried by the wrench for exerting a bearing force in a direction along said axis on the measuring cell, and means for preventing the wrench from driving the measuring cell in rotation during the tightening.

2. A device according to claim 1, wherein the resiliently yieldable means carried by the wrench comprise a leaf spring having a curved end portion in bearing relation to an upper planar surface of the measuring cell during the tightening, the curved portion of the leaf spring being rotatable relative to the cell with a slight friction therebetween.

3. A device according to claim 1, wherein said cell includes a shoulder and said detector is mounted to be slidable in a direction along said axis inside the measuring cell and includes stop means which are adapted to bear against said shoulder when the device is withdrawn from the nut, a spring interposed between said cell and said detector exerting a bearing force on the detector for causing the detector to bear against the pin when the tightening device is in use.

* * * * *